United States Patent [19]

Bohn et al.

[11] Patent Number: 4,888,333
[45] Date of Patent: Dec. 19, 1989

[54] ALLYMERCAPTOACETYLSYDNONIMINES, PROCESSES FOR THEIR PREPARATION, AND THEIR USE

[75] Inventors: Helmut Bohn; Melitta Just, both of Schöneck; Rolf-Eberhard Nitz, Frankfurt, all of Fed. Rep. of Germany

[73] Assignee: Cassella Aktiengesellschaft, Frankfurt, Fed. Rep. of Germany

[21] Appl. No.: 230,846

[22] Filed: Aug. 10, 1988

Related U.S. Application Data

[63] Continuation of Ser. No. 133,543, Dec. 16, 1987, abandoned.

[30] Foreign Application Priority Data

Jan. 24, 1987 [DE] Fed. Rep. of Germany ....... 3702083

[51] Int. Cl.⁴ ................ C07D 271/04; C07D 413/04; A61K 31/41
[52] U.S. Cl. .................................... 514/212; 514/252; 514/326; 514/364; 514/227.8; 514/236.2; 540/524; 544/60; 544/138; 544/367; 546/209; 548/125
[58] Field of Search ........................ 548/125; 546/209; 544/60, 138, 167; 540/524; 514/212, 222, 232, 252, 326, 364

[56] References Cited

FOREIGN PATENT DOCUMENTS 276710 8/1988 European Pat. Off. ............ 548/125

*Primary Examiner*—Robert Gerstl
*Attorney, Agent, or Firm*—Perman & Green

[57] ABSTRACT

Substituted allylmercaptoacetylsydnonimines of the general formula I

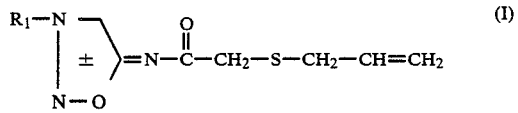

and their pharmacologically acceptable acid addition salts, in which $R_1$ represents a secondary amino group of the formula

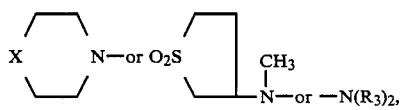

and
X denotes

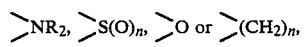

$R_2$ denotes one of the radicals $R_3OOC-$, $R_4SO_2-$ or alkyl having 1-4 C atoms,
n denotes one of the values 1, 1 or 2,
and $R_3$ denotes alkyl having 1-4 C atoms,
and $R_4$ represents $R_3$ or $(R_3)_2N-$, have valuable pharmacological properties.

6 Claims, No Drawings

ALLYMERCAPTOACETYLSYDNONIMINES, PROCESSES FOR THEIR PREPARATION, AND THEIR USE

This application is a continuation of co-pending application Ser. No. 133,543 filed Dec. 16, 1987, now abandoned.

The invention relates to pharmacologically active substituted allylmercaptoacetylsydnonimines of the general formula

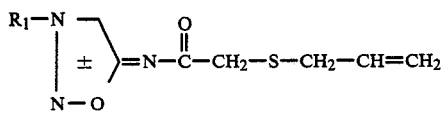
(I)

in which $R_1$ represents a secondary amino group of the formula

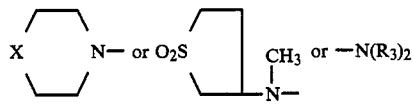

and
X denotes

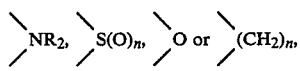

$R_2$ denotes one of the radicals $R_3OOC-$, $R_4SO_2-$, or alkyl having 1–4 C atoms, n denotes one of the values 0, 1 or 2, and $R_3$ denotes alkyl having 1–4 C atoms, and $R_4$ represents $R_3$ or $(R_3)_2N-$, and to their pharmacologically acceptable salts.

The invention also relates to processes for the preparation of these allylmercaptoacetylsydnonimine derivatives and their salts, and to their use as pharmaceutical active compounds.

Particularly preferred radicals $R_1$ are:

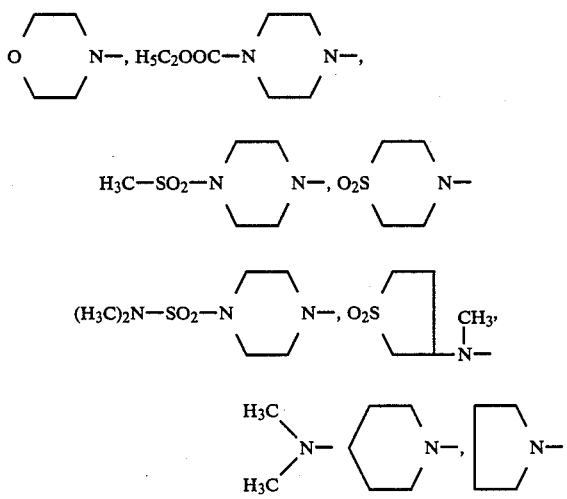

$R_1$ is particularly preferably the morpholino radical. The alkyl radicals represented by $R_3$ and $R_4$ can be straight-chain or branched.

The allylmercaptoacetylsydnonimines of the general formula I, according to the invention, can be obtained by various processes which are known per se. These processes are characterized in that (a) a sydnonimine of the general formula II

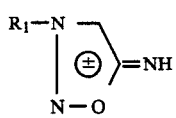
(II)

where appropriate in the form of a salt, is reacted with an acylating agent which introduces the allylmercaptoacetyl radical, or (b) a sydnonimine of the general formula II, where appropriate in the form of a salt, is acylated with an acetic acid derivative which contains a radical which is subsequently reacted with allyl mercaptan to give the allylmercapto compound of the general formula I.

The preparation of the compounds of the formula II which are used as starting materials

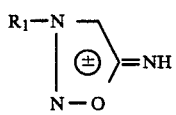
(II)

in which $R_1$ has the said meanings, is described in, for example, European Patent Specifications 23343 and 59356.

The acylation of the compounds of the formula II to introduce the radicals

Z denoting a group which can be replaced by the radical $-S-CH_2-CH=CH_2$, can be carried out in a manner known per se, using suitable acylating agents of the formulae IIIa and b

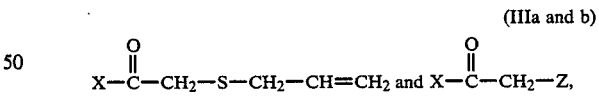
(IIIa and b)

in which X denotes, for example, halogen, in particular chlorine, aryloxy, in particular tolyloxy, dinitrophenyloxy or nirophenyloxy, or O-acyl with the same acyl radical (that is to say an acid anhydride). Z can denote, in particular, halogen, $OSO_2CH_3$ or $OSO_2Ar$, Ar representing an optionally substituted phenyl radical.

The reaction between the acylating agent and the compound II is expediently carried out in the liquid phase in the presence of an inert solvent, dispersant or diluent.

Examples of suitable solvents, dispersants or diluents are alcohols, in particular those having 1 to 6 C atoms such as, for example, methanol, ethanol, i- and n-propanol, i-, sec.- and tert.-butanol, n-, i-, sec.- and tert.-pentanol, n-hexanol, cyclopentanol and cyclohexanol;

ethers, in particular those having 2 to 8 C atoms in the molecule, such as, for example, diethyl ether, methyl ethyl ether, di-n-propyl ether, diisopropyl ether, methyl n-butyl ether, ethyl propyl ether, dibutyl ether, tetrahydrofuran, 1,4-dioxane, 1,2-dimethoxyethane and bis-$\beta$-methoxyethyl ether; polyethers such as, for example, polyethylene glycols having a molecular weight up to about 600; oligoethylene glycol dimethyl ethers such as, for example, pentaglyme; crown ethers, that is to say cyclic polymers of ethylene glycol of the formula ($-OCH_2CH_2)_p$, p being a number from 4 to 10, for example, it also being possible for one or more benzene rings to be fused onto the ring; aza- and thiacrown ethers (coronand amines and coronand sulphides); glycols and partially etherified glycols, such as, for example, ethylene glycol, propylene glycol, trimethylene glycol, ethylene glycol monomethyl ether, ethylene glycol monoethyl ether and diethylene glycol monoethyl ether; aliphatic hydrocarbons such as, for example, petroleum spirits, low- and high-boiling petroleum ethers, aromatic hydrocarbons such as, for example, benzene, toluene, o-, m- and p-xylene, pyridine; halogenated aliphatic or aromatic hydrocarbons such as, for example, methylene chloride, chloroform, carbon tetrachloride, ethylene chloride, chlorobenzene or dichlorobenzene; nitriles such as, for example, acetonitrile; amides, such as, for example, dimethylformamide or N-methylpyrrolidione; sulphoxides such as, for example, dimethyl sulphoxide; water. It is also possible to use mixtures of various solvents, dispersants or diluents, for example water/methylene chloride or water/toluene. It is also possible to use an excess of the acylating agent as solvent, dispersant or diluent.

The alcohols, glycols and partially etherified glycols mentioned as solvents, dispersants or diluents, as well as water, are normally suitable only for the acylating with carboxylic esters, whereas for carrying out the acylation with other acylating agents they are insufficiently inert, because of the competing formation of esters, glycol esters or acids, and thus are less suitable.

The molar ratio between the compound of the formula II and the acylating agent is 1:1. It is expedient for the acylating agent to be used in a small molar excess. Excesses of up to 30 mol-% are sufficient as a rule, that is to say the molar ratio between the compound of the formula II and the acylating agent is normally 1:(1 to 1.3), preferably 1:(1 to 1.2). If an acid is eliminated during the acylation reaction, it is expedient to add an acid trap such as, for example, an alkali metal hydroxide such as, for example, sodium, potassium or lithium hydroxide, a tertiary organic amine such as, for example, pyridine or triethylamine, an alkali metal carbonate or alkali metal bicarbonate such as, for example, sodium carbonate or sodium bicarbonate, or an alkali metal salt of a weak organic acid such as, for example, sodium acetate. It is also possible to add suitable catalysts in the acylation reaction, such as, for example, 4-dimethylaminopyridine.

The reaction between the acylating agent and the compound II can, in principle, be carried out at temperatures between $-10°$ C. and the boiling point of the solvent, dispersant or diluent used. In many cases, the reaction will be carried out at 0° to 50° C., in particular at 0° to 30° C. and, preferably, at room temperature.

The substituted allylmercaptoacetylsydnonimines of the general formula I form acid addition salts with inorganic or organic acids. Inorganic and organic acids are suitable for the formation of acid addition salts of this type. Examples of suitable acids are hydrogen chloride, hydrogen bromide, naphthalenedisulphonic acids, in particular naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts can be prepared as customary by mixing the components, expediently in a suitable solvent or diluent. In the synthesis of the compounds of the formula I, the latter may result in the form of the acid addition salts. The free compounds of the general formula I can, if desired, be obtained from the acid addition salts in a known manner, that is to say by dissolving or suspending in water and making alkaline, for example with sodium hydroxide solution, followed by isolation.

The requisite starting compounds of the general formula II can be prepared in a manner known per se, using Strecker's amino nitrile synthesis, from compounds of the general formula

$$R_1-NH_2$$

by reaction with formaldehyde and hydrocyanic acid or sodium cyanide in a suitable solvent, for example water, there being initial formation of a compound of the general formula

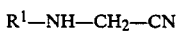

$$R^1-NH-CH_2-CN$$

which is then subjected to nitrosation. The nitrosation is carried out in a known manner in a suitable solvent, preferably in water, at temperatures of 0° to 10° C. The nitrous acid for this is normally generated from an alkali metal nitrite and hydrochloric acid. It is expedient to adjust the pH of the aqueous solution of the compound of the formula $R^1-NH-CH_2-CN$ to 1 to 3 using hydrochloric acid, and to add the alkali metal nitrite, in the form of an aqueous solution, dropwise to the stirred and cooled solution of the compound.

The solution of the resulting nitroso compound can be directly subjected to the cyclization reaction. However, it is normally appropriate for the nitroso compound first to be taken up in a suitable organic solvent, and for the cyclization to give the compound of the formula II to be carried out therein, where appropriate after addition of another solvent.

The compounds of the general formula I and their pharmacologically acceptable acid addition salts have valuable pharmacological properties.

Their action on the caridovascular system is particularly pronounced. Compared with the compound molsidomine, which is commercially available and has a similar structure, they act at lower doses and over an even longer period.

Thus the compounds of the formula I and their pharmacologically acceptable acid addition salts can be administered to humans as medicines on their own, in mixtures with one another, or in the form of pharmaceutical formulations which allow enteral or parenteral administration and contain, as active ingredient, an effective dose of at least one compound of the formula I, or of an acid addition salt thereof, in addition to customary pharamaceutically acceptable vehicles and additives.

The medicines can be administered orally, for example in the form of pills, tablets, lacquered tablets, sugar-coated tablets, hard and soft gelatin capsules, solutions, syrups, emulsions or suspensions, or aersol mixtures. However, it is also possible for administration to take place rectally, for example in the form of suppositories, or parenterally, for example in the form of injection solutions, or percutaneously, for example in the form of ointments or tinctures.

Pharmaceutically inert inorganic or organic vehicles can be used to prepare the pharmaceutical products. For the preparation of pills, tablets, sugar-coated tablets and hard gelating capsules it is possible to use, for example, lactose, maize starch or derivatives thereof, talc, stearic acid or its salts etc. Examples of vehicles for soft gelatin capsules and suppositories are fats, waxes, semi-solid and liquid polyols, natural or hardened oils etc. Examples of suitable vehicles for the preparation of solutions and syrups are water, sucrose, invert sugar, glucose, polyols etc. Examples of suitable vehicles for the preparation of injection solutions are water, alcohols, glycerol, polyols, vegetable oils etc.

In addition to the active substances and vehicles, the pharmaceutical products can also contain additives such as, for example, fillers, extenders, disintegrants, binders, lubricants, wetting agents, stabilizers, emulsifiers, preservatives, sweeteners, colorants, flavourings or aromatizing agents, thickeners, diluents or buffer substances, as well as solvents or solubilizers or agents for achieving a depot effect, and salts to alter the osmotic pressure, coating agents or antioxidants. They can also contain two or more compounds of the formula I, or their pharmacologically acceptable acid addition salts, as well as other therapeutically active substances.

Examples of other therapeutically active substances of this type are: β-receptor blockers such as, for example, propranolol, pindolol and metoprolol; vasodilators such as, for example, carbocromen; tranquillizers such as, for example, barbituric acid derivatives, 1,4-benzodiazepines and meprobamate; diuretics such as, for example, chlorothiazide; cardiotonic agents such as, for example, digitalis products; agents lowering blood pressure, such as, for example, hydralazine, dihydralazine, prazosin, clonidine and rauwolfia alkaloids; agents which lower the level of fatty acids in the blood, such as, for example, bezafibrate and fenofibrate; and agents for the prophylaxis of thrombosis, such as, for example, phenoprocoumon.

The compounds of the formula I, their pharmacologically acceptable acid addition salts, and pharmaceutical products which contain the compounds of the formula I or their pharmacologically acceptable acid addition salts as active substances can be used in humans for controlling or preventing diseases of the cardiovascular system, for example as antihypertensive medicines for the various types of high blood pressure, and for controlling and preventing angina pectoris. The dosage can vary within wide limits and should be adjusted to suit the individual circumstances in each particular case. In general, on oral administration an appropriate daily dose per human individual is from about 0.5 to 100 mg, preferably 1 to 20 mg. With other types of administration too, because of the good absorption of the active compounds the daily dose is in similar ranges of amounts, that is to say in general likewise 0.5 to 100 mg/person. The daily dose is normally divided into several, for example 2 to 4, parts for administration.

The examples which follow serve to explain the invention in more detail.

EXAMPLE 1

3-Morpholino-N-allylmercaptoacetylsydononimine 2 g of allyl mercaptan are dissolved in 50 ml of methanol and, under nitrogen, 6 g of 3-morpholino-N-chloroacetylsydnonimine are added. A solution of 2.7 g of potassium tert.butylate in 20 ml of methanol is added dropwise, and the mixture is stirred under nitrogen at room temperature for 12 hours.

After an insoluble byproduct has been filtered off, the reaction solution is concentrated in vacuo, the residue is taken up in ethyl acetate, and the solution is again filtered and concentrated. The residue obtained from this is finally stirred with ether, filtered off with suction and dried.

Yield: 4.0 g of 3-morpholino-N-allymercaptoacetylsydnonimine

Melting point = 83°–84° C.

EXAMPLE 2

3-(4-Ethoxycarbonyl-1-piperazinyl)-N-allylmercaptoacetylsydnonimine

A solution of 5.6 g of 3-(4-ethoxycarbonyl-1-piperazinyl)sydnonimine hydrochloride in 50 ml of water is cooled to 5° C. 4.2 g of solid sodium bicarbonate are added, and a solution of 3.8 g of allylmercaptoacetyl chloride in 50 ml of methylene chloride is added to the reaction mixture. The mixture is stirred at room temperature for 3 hours. The organic phase is separated off, dried over sodium sulphate and concentrated in a rotary evaporator. The residue is stirred with ether. The resulting solid is filtered off with suction and recrystallized from ethyl acetate.

Yield: 5.9 g of 3-(4-ethoxycarbonyl-1-piperazinyl)-N-allylmercaptoacetylsydnonimine.

Melting point = 96°–97° C.

The following products are prepared in a manner analogous to that described in Example 1 and 2:

EXAMPLE 3

3-(4-Methylsulphonyl-1-piperazinyl)-N-allylmercaptoacetylsydnonimine.

Melting point = 102°–103° C.

EXAMPLE 4

3-(4-Dimethylaminosulphonyl-1-piperazinyl)-N-allylmercaptoacetylsydnonimine.

Melting point = 79°–80° C.

EXAMPLE 5

3-(1,1-Dioxotetrahydro-1,4-thiazin-4-yl)-N-allylmercaptoacetylsydnonimine.

Melting point = 109°–110° C.

EXAMPLE 6

3-(N-Methyl-N-1,1-dioxotetrahydro-3-thienylamino)-N-allylmercaptoacetylsydnonimine.

Melting point = 105°–106° C.

EXAMPLE 7

3-Dimethylamino-N-allylmercaptoacetylsydnonimine.

Melting point = 100°–101° C.

EXAMPLE 8

3-Piperidino-N-allylmercaptoacetylsydnonimine.
Melting point=97°-98° C.

EXAMPLE 9

3-Pyrrolidino-N-allylmercaptoacetylsydnonimine.
Melting point=108°-109° C.

The examples which follow relate to pharmaceutical formulations.

Example A

| Tablets | per tablet |
| --- | --- |
| 3-Substituted N—allylmercaptoacetyl-sydnonimine according to the invention | 20 mg |
| Lactose | 60 mg |
| Maize starch | 30 mg |
| Soluble starch | 5 mg |
| Magnesium stearate | 5 mg |
| | 120 mg |

Example B

| Sugar-coated tablet | |
| --- | --- |
| 3-Substituted N—allylmercaptoacetyl-sydnonimine according to the invention | 6 mg |
| Propranolol | 40 mg |
| Lactose | 90 mg |
| Maize starch | 90 mg |
| sec. Calcium phosphate | 34 mg |
| | 260 mg |

Example C

| Capsules | |
| --- | --- |
| 3-Substituted N—allylmercaptoacetyl-sydnonimine according to the invention | 5 mg |
| Prazosin | 5 mg |
| Maize starch | 185 mg |
| | 195 mg |

Example D

| Injection solution | |
| --- | --- |
| 3-Substituted N—allylmercaptoacetyl-sydnonimine according to the invention | 4 mg |
| Sodium chloride | 0.7 mg |
| Water for injections ad | 1 ml |

Example E

| Suppositories | |
| --- | --- |
| 3-Substituted N—allylmercaptoacetyl-sydnonome according to the invention | 20 mg |
| Suppository base ad | 1 g |

The pharmacological action of the compounds of the formula I was established using a modification of the method of Godfraind and Kaba (Arch. Int. Pharmacodyn. Ther. 196, (Suppl) 35 to 49, 1972) and of Schümann et al. (Naunyn-Schmiedeberg's Arch. Pharmacol. 289, 409 to 481, 1975). This entails spiral strips of the pulmonary artery of the guinea pig being equilibrated in calcium-free Tyrode's solution and then depolarized with 40 mmol/l of potassium. Addition of 0.5 mmol/l of $CaCl_2$ then triggers a contraction. The relaxant effect of the test substance is established by cumulative addition of concentrations in ½ log 10 steps. The concentration of the test substance which inhibits contraction by 50% (=$IC_{50}$, mol/l) is established from the concentration/effect graph (abscissa: −log mol/l test substance, ordinate: % inhibition of the maximum contraction, mean of 4 to 6 vessel strips). The $IC_{50}$ values obtained in this way are shown in the table which follows. Comparison with the $IC_{50}$ of $1 \times 10^{-4}$ for the known compound molsidomine (N-ethoxycarbonyl-3-morpholinosydnonimine), see DE-B 16 70 827, reveals that the values for the compounds of the formula I are considerably more favourable.

TABLE

| Compound of the formula I according to Example | $IC_{50}$ (mol/l) |
| --- | --- |
| 1 | $2 \times 10^{-5}$ |
| 2 | $8 \times 10^{-5}$ |
| 3 | $3 \times 10^{-5}$ |
| 4 | $3 \times 10^{-5}$ |
| 5 | $3 \times 10^{-5}$ |
| 6 | $1 \times 10^{-5}$ |
| 7 | $3 \times 10^{-5}$ |
| 8 | $2 \times 10^{-5}$ |
| Molsidomine (N—Ethoxycarbonyl-3-morpholino-sydnonimine) (Comparison substance) | $>1 \times 10^{-4}$ |

What we claim is

1. Allylmercaptoacetylsydnonimines of the general formula I $$R_1-N \diagdown \phantom{xx} \diagup \phantom{x} =N-\overset{O}{\underset{\|}{C}}-CH_2-S-CH_2-CH=CH_2 \qquad (I)$$
$$\phantom{xxxxx} \pm$$
$$\phantom{xx} N-O$$

in which $R_1$ is a secondary amino radical selected from the group consisting of $$X \diagup \diagdown N- \text{ or } O_2S \diagup \diagdown \phantom{x} \underset{\underset{N-}{|}}{CH_3}, \text{ and } -N(R_3)_2$$

and X is a radical selected from the group consisting of $$>NR_2, >S(O)_n, >O \text{ and } >(CH_2)_n,$$

$R_2$ is a radical selected from the group consisting of $R_3OOC-$, $R_4SO_2-$, and alkyl having 1-4 C atoms, n denotes one of the values 0, 1 or 2, and $R_3$ is an alkyl radical having 1-4 C atoms, and $R_4$ is a radical selected from the group consisting of $R_3$ and $(R_3)_2N-$, and their pharmacologically acceptable salts.

2. Allylmercaptoacetylsydnonimines according to claim 1, characterized in that $R_1$ denotes the radical

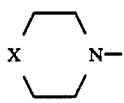

and X is a radical selected from the group consisting of $>NR_2$, $>SO_2$, and $>O$, and $>R_2$ is a radical selected from the group consisting of $R_3OOC-$ and $R_4SO_2-$, and $R_3$ is a radical selected from the group consisting of methyl and ethyl, and $R_4$ is a radical selected from the group consisting of methyl, ethyl, dimethylamino and diethylamino.

3. Allylmercaptoacetylsydnonimines according to claim 1, characterized in that $R_1$ is

4. Allylmercaptoacetylsdnonimines according to claim 2 characterized in that $R_1$ is

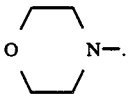

5. Medicament formulation for the treatment of thromboembolic diseases of the heart and circulatory system containing, besides the customary auxiliaries and excipients used in galenics, an effective dose of an allylmercaptoacetylsydnonimine as defined in claim 1.

6. Process for treatment of thromboembolic diseases of the heart and circulatory system comprising administering to a patient in need thereof a pharmacologically effective dose of a allylmercaptoacetylsydnonimine as defined in claim 1.

* * * * *

UNITED STATES PATENT AND TRADEMARK OFFICE
CERTIFICATE OF CORRECTION

PATENT NO. : 4,888,333

DATED : December 19, 1989

INVENTOR(S) : Schonafinger et al.

It is certified that error appears in the above-identified patent and that said Letters Patent is hereby corrected as shown below:

The title on page 1, lines 1-3 should read "Allylmercaptoacetylsydnonimines, Medicament Formulations and Process For Use";

Also, the Inventors line on page 1, line 4 should read:

Karl Schonafinger, Alzenau; Rudi Beyerle, Frankfurt; Helmut Bohn; Melitta Just, both of Schöneck; Rolf-Eberhard Nitz, Frankfurt, all of Fed. Rep. of Germany Signed and Sealed this Twenty-ninth Day of January, 1991

Attest:

HARRY F. MANBECK, JR.

*Attesting Officer*  *Commissioner of Patents and Trademarks*